United States Patent
Neumann

(10) Patent No.: US 12,354,754 B2
(45) Date of Patent: *Jul. 8, 2025

(54) METHODS AND SYSTEMS FOR OPTIMIZING SUPPLEMENT DECISIONS

(71) Applicant: KPN Innovations, LLC.

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 109 days.

This patent is subject to a terminal disclaimer.

(21) Appl. No.: 16/886,481

(22) Filed: May 28, 2020

(65) Prior Publication Data

US 2021/0166818 A1 Jun. 3, 2021

Related U.S. Application Data

(63) Continuation-in-part of application No. 16/699,407, filed on Nov. 29, 2019, now Pat. No. 10,734,096.

(51) Int. Cl.
*G06N 20/00* (2019.01)
*G16B 40/30* (2019.01)
(Continued)

(52) U.S. Cl.
CPC ............. *G16H 50/30* (2018.01); *G06N 20/00* (2019.01); *G16B 40/30* (2019.02); *G16H 20/60* (2018.01)

(58) Field of Classification Search
CPC ........ G16H 20/60; G16H 20/10; G16H 10/60; G16H 50/30; G06F 19/3475;
(Continued)

(56) References Cited

U.S. PATENT DOCUMENTS 5,347,453 A * 9/1994 Maestre ................. A61J 7/0481
705/2
5,954,640 A * 9/1999 Szabo .................... G16H 10/60
600/300

(Continued)

FOREIGN PATENT DOCUMENTS

| WO | 2010030600 | 3/2010 | |
| WO | 2018204763 | 11/2018 | |
| WO | WO-2018204763 A2 * | 11/2018 | ............. G06Q 30/02 |

OTHER PUBLICATIONS

Huang et al., "Prediction of Microbe-Disease Association from the Integration of Neighbor and Graph with Collaborative Recommendation Model", 2017, Journal of Translational Medicine, pp. 1-11 (Year: 2017).*

(Continued)

*Primary Examiner* — Paulinho E Smith
(74) *Attorney, Agent, or Firm* — Caldwell Intellectual Property Law

(57) ABSTRACT

A system for optimizing supplement decisions is disclosed. The system includes a computing device configured to receive a longevity inquiry from a remote device. The system retrieves a biological extraction pertaining to a user and identifies a longevity element associated with a user. The system selects an ADME model utilizing a biological extraction. The system generates a machine-learning algorithm utilizing the selected ADME model to input a longevity element associated with a user as an input and output an ADME factor. The system identifies a second longevity element compatible with the ADME factor as a function of the first longevity element. The system selects the second longevity element as a tolerant longevity element. A method for optimizing supplement decisions is also disclosed.

20 Claims, 9 Drawing Sheets

(51) Int. Cl.
*G16H 20/60* (2018.01)
*G16H 50/30* (2018.01)

(58) Field of Classification Search
CPC ............ G06F 16/9535; G06F 19/3456; G06Q 30/0631; G06Q 30/0269; G09B 19/0092; G16B 40/30; G06N 20/00
See application file for complete search history.

(56) References Cited

U.S. PATENT DOCUMENTS

| | | | | |
|---|---|---|---|---|
| 7,136,820 | B1* | 11/2006 | Petrus | G16H 20/60 600/300 |
| 7,809,601 | B2* | 10/2010 | Shaya | G06Q 30/0641 705/26.7 |
| 7,953,613 | B2* | 5/2011 | Gizewski | G16H 40/60 705/2 |
| 7,990,251 | B1* | 8/2011 | Ford, Jr. | G16H 40/67 715/767 |
| 10,332,418 | B2* | 6/2019 | Hardee | G01N 33/0047 |
| 10,553,319 | B1* | 2/2020 | Neumann | G06N 7/005 |
| 10,559,386 | B1* | 2/2020 | Neumann | G06N 20/10 |
| 2003/0069757 | A1* | 4/2003 | Greenberg | G16H 20/60 705/2 |
| 2004/0193446 | A1* | 9/2004 | Mayer | G16H 10/20 600/300 |
| 2006/0047538 | A1* | 3/2006 | Condurso | G16H 40/67 705/3 |
| 2007/0143126 | A1* | 6/2007 | Ghose | G16H 20/60 434/127 |
| 2007/0174088 | A1* | 7/2007 | Koo | G06Q 30/02 705/28 |
| 2008/0162352 | A1* | 7/2008 | Gizewski | G16H 50/20 705/50 |
| 2008/0275912 | A1* | 11/2008 | Roberts | G16B 20/00 |
| 2011/0014351 | A1* | 1/2011 | Reider | G16H 10/20 53/473 |
| 2011/0054928 | A1* | 3/2011 | Sullivan | G16H 20/60 705/2 |
| 2013/0023058 | A1* | 1/2013 | Toumazou | G16H 10/20 436/501 |
| 2013/0261183 | A1* | 10/2013 | Bhagat | A61P 43/00 426/71 |
| 2014/0067425 | A1* | 3/2014 | Dudar | G16Z 99/00 705/3 |
| 2014/0121990 | A1* | 5/2014 | Baldi | G16B 50/30 702/20 |
| 2014/0136362 | A1* | 5/2014 | Shaya | G06Q 30/02 705/26.7 |
| 2015/0012295 | A1 | 1/2015 | Mahoney | |
| 2017/0098056 | A1* | 4/2017 | Reddy | G16H 20/13 |
| 2017/0148348 | A1* | 5/2017 | Hardee | G09B 19/0092 |
| 2017/0236337 | A1* | 8/2017 | Devries | G06F 3/013 345/419 |
| 2018/0052885 | A1* | 2/2018 | Gaskill | G06N 5/04 |
| 2018/0135122 | A1* | 5/2018 | Hilden | G16B 40/00 |
| 2018/0144820 | A1* | 5/2018 | Grimmer | G06F 16/9535 |
| 2018/0211723 | A1* | 7/2018 | Coles | G16H 20/60 |
| 2019/0154648 | A1* | 5/2019 | Lawrence | A61K 9/08 |
| 2019/0172575 | A1* | 6/2019 | Reddy | H04M 1/72412 |
| 2020/0000270 | A1* | 1/2020 | Iotti | A47J 31/461 |
| 2020/0270699 | A1* | 8/2020 | Mir | C12Q 1/6883 |

OTHER PUBLICATIONS

"Baze; Personalized Vitamins Based on a Convenient Blood Test"; Nov. 7, 2019; https://www.baze.com/how-it-works/ retrieved Nov. 7, 2019.

"Using DNA Test Results, This Company Makes Customized Vitamins Specifically for You" Futurism Creative; Jun. 9, 2019; https://futurism.com/neoscope/dna-test-personalized-vitamins retrieved Nov. 7, 2019.

"This Company Will Tell You Which Vitamins and Supplements to Take Base don Your DNA"; Sarah Buhr; Feb. 5, 2018; https://techcrunch.com/2018/02/05/this-company-will-tell-you-which-vitamins-and-supplements-to-take-based-on-your-dna/2018/02/05/this-company-will-tell-you-which-vitamins-and-supplements-to-take-based-on-your-dna/ retrieved Nov. 7, 2019.

* cited by examiner

METHODS AND SYSTEMS FOR OPTIMIZING SUPPLEMENT DECISIONS

CROSS-REFERENCE TO RELATED APPLICATIONS

This continuation-in-part application claims the benefit of priority of U.S. Non-Provisional patent application Ser. No. 16/699,407, filed on Nov. 29, 2019 and entitled "METHODS AND SYSTEMS FOR OPTIMIZING SUPPLEMENT DECISIONS", which is incorporated by reference herein in its entirety.

FIELD OF INVENTION

The present invention generally relates to the field of artificial intelligence. In particular, the present invention is directed to methods and systems for optimizing supplement decisions.

BACKGROUND

Accurate and ideal selection of supplements can be challenging and often require a multi-factorial approach. Frequently consumers are unaware about how supplements may be metabolized and distributed throughout their bodies. This can often lead to ill-fitting information that can have potentially deadly consequences. Currently there is an unmet need to strap consumers with such knowledge. The present invention generally relates to the field of artificial intelligence. In particular, the present invention is directed to methods and systems for optimizing supplement decisions.

SUMMARY OF THE DISCLOSURE

In an aspect, a system for optimizing supplement decisions is disclosed. The system includes a computing device, the computing device further configured to receive a longevity inquiry from a remote device. The system is further configured to retrieve a biological extraction from a user database. The system is further configured to identify a first longevity element associated with a user as a function of the longevity inquiry and the biological extraction. The system is further configured to select an ADME model as a function of the biological extraction. The system is further configured to generate a machine-learning algorithm utilizing the ADME model that inputs the longevity element associated with the user as an input and outputs an ADME factor. The system is further configured to identify a second longevity element compatible with the ADME factor. The system is further configured to select the second longevity element as a tolerant longevity element.

In an aspect, a method of optimizing supplement decisions is disclosed. The method includes receiving by a computing device a longevity inquiry from a remote device. The method includes retrieving by the computing device a biological extraction from a user database. The method includes identifying by the computing device a first longevity element associated with a user as a function of the longevity inquiry and the biological extraction. The method includes selecting by the computing device an ADME model as a function of the biological extraction. The method includes generating by the computing device a machine-learning algorithm utilizing the ADME model that inputs the longevity element associated with the user as an input and outputs an ADME factor. The method includes identifying a second longevity element compatible with the ADME factor. The method includes selecting the second longevity element as a tolerant longevity element.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for optimizing supplement decisions. In an embodiment, a computing device receives a longevity inquiry from a remote device. A longevity inquiry may include a question or remark as to the best supplement that a user can consume. A longevity inquiry may include a picture or photograph of a particular brand of supplement. A computing device utilizes a user's biological extraction in combination with a longevity inquiry to identify a first longevity element associated with the user. A longevity element may include a particular brand of supplement or category of supplement. For example, a longevity element may include fish oil, or a longevity element may include a category of supplements such as anti-inflammatories, joint support, or heart health. A computing device selects an ADME model utilizing a biological extraction and generates a machine-learning algorithm utilizing the ADME model to input a longevity element associated with the user as an input and outputs an ADME factor. A computing device identifies a tolerant longevity element utilizing an ADME factor. An ADME factor provides insights as to how a user may best absorb, distribute, metabolize, and eliminate one or more longevity elements. For example, an ADME factor may indicate that a user has altered renal elimination and as such may need to consume a longevity element that is hepatically eliminated. The computing device identifies a second longevity element compatible with the ADME factor. The computing device selects the second longevity element as a tolerant longevity element.

Figure 1:
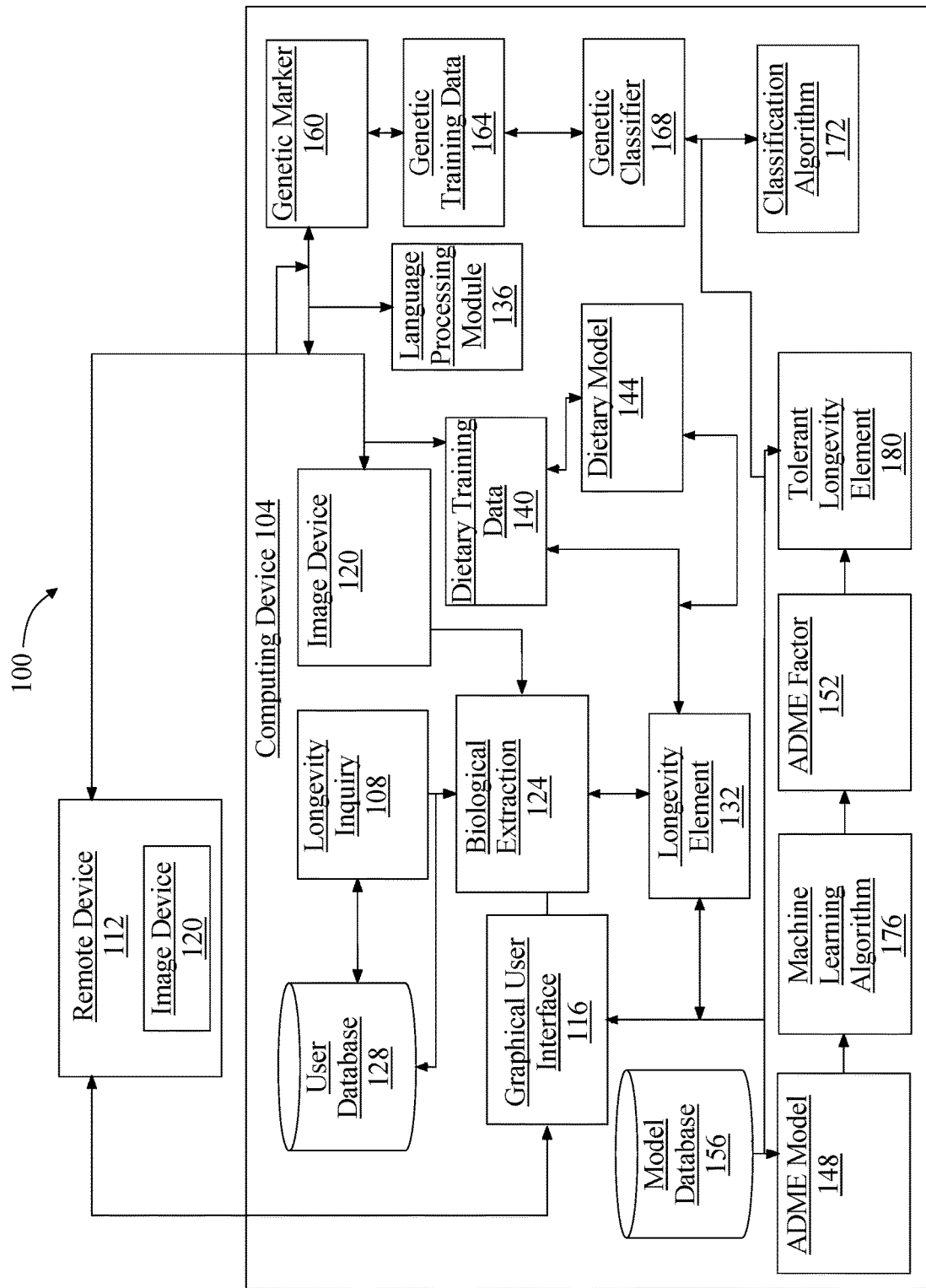
FIG. 1 is a block diagram illustrating an exemplary embodiment of a system for optimizing supplement decisions.

Referring now to FIG. 1, an exemplary embodiment of a system 100 for optimizing supplement decisions is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a longevity inquiry 108 from a remote device 112. A "longevity inquiry 108" as used in this disclosure, includes any inquiry generated by a user regarding a supplement or longevity element. inquest A "longevity element" as used in this disclosure, includes any supplement intended to supplement the diet of a human being and/or animal. Supplements may include products consumed by a user that contain a dietary ingredient. Dietary ingredients may include any vitamin, mineral, nutrient, homeopathic, amino acid, herb, botanical, nutraceutical, enzyme, health food, medical food, and the like. Supplements may contain dietary ingredients sourced from food, synthesized in a laboratory, and/or sourced in combination. Supplements may include for example, a multi-vitamin, co-enzyme q10, ubiquinol, resveratrol, probiotics such as *Lactobacillus Acidophilus, Bifidobacterium Bifidum, Saccharomyces Boulardii*, fish oil, B-Vitamin complex, Vitamin D, cranberry, products containing combination ingredients, and the like. Supplements may be available in a variety of different dosage forms for a user to consume including for example, capsules, tablets, pills, buccal tablets, sub-lingual tablets, orally-disintegrating products, thin films, liquid solution, liquid suspension, oil suspension, powder, solid crystals, seeds, foods, pastes, buccal films, inhaled forms such as aerosols, nebulizers, smoked forms, vaporized form, intradermal forms, subcutaneous forms, intramuscular forms, intraosseous forms, intraperitoneal forms, intravenous forms, creams, gels, balms, lotion, ointment, ear drops, eye drops, skin patch, transdermal forms, vaginal rings, dermal patch, vaginal suppository, rectal suppository, urethral suppository, nasal suppository, and the like. Supplements may be available to a user without a prescription such as for example, a fish oil supplement sold at a health food store. In an embodiment, supplements may be selected and/or identified after identifying a user's food supply, where a food supply includes any food and/or beverage consumed by a human being. Supplements may be available to a user with a prescription, such as for example subcutaneous cyanocobalamin injections available at a compounding pharmacy. Supplements may be categorized into different grade products such as for example pharmaceutical grade supplements that may contain in excess of 99% purity and do not contain binders, fillers, excipients, dyes, or unknown substances and are manufactured in Food and Drug Administration (FDA) registered facilities that follow certified good manufacturing practices (cGMP); supplements may be of food grade quality such as for example supplements deemed to be suitable for human consumption; supplements may be of feed grade quality such as for example supplements deemed to be suitable for animal consumption. A longevity element may include a particular supplement product such as a particular brand name supplement. A longevity element may include a particular category of supplement such as supplements to support heart health, immune health, women's health, joint health and the like. A longevity element may include a generic supplement not necessarily associated with any particular brand name such as a fish oil supplement, coenzyme q10 supplement, and the like.

With continued reference to FIG. 1, an inquest in regard to a longevity element may include one or more questions, problems, issues, and/or inquiries regarding a longevity element. A user may pose a general question about what particular supplements the user should be taking. A user may pose a question about a particular supplement such as how much Vitamin D a user should be taking. A user may describe one or more symptoms that the user may be experiencing to inquire about one or more supplements that may diminish, reduce, and/or eliminate one or more symptoms. For example, a user may describe symptoms such as a headache, runny nose, fatigue, and a productive cough and generate a longevity inquiry 108 describing such symptoms and ask what supplements may reduce and/or diminish such symptoms. A user may generate a longevity inquiry 108 based on an encounter with one or more informed advisors. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like. For instance and without limitation, an informed advisor such as a user's nutritionist may recommend that user consume a Vitamin B12 supplement because user has recently started a vegetarian diet. In such an instance, user may generate a longevity inquiry 108 to inquire about what Vitamin B12 supplement user should take, what form of Vitamin B12 user should consume such as cyanocobalamin versus hydroxocobalamin and methylcobalamin, how frequently the user should consume the Vitamin B12, and what dosage form of Vitamin B12 user should consume.

With continued reference to FIG. 1, computing device 104 receives a longevity inquiry 108 from a remote device 112. Remote device 112 may include without limitation, a display in communication with computing device 104, where a display may include any display as described herein. Remote device 112 may include an additional computing device, such as a mobile device, laptop, desktop, computer and the like. Remote device 112 may transmit and/or receive one or more inputs from computing device 104 utilizing any network methodology as described herein. Remote device 112 may be operated by a user which may include any human subject. Remote device 112 may be operated by an informed advisor. Remote device 112 may be operated by a family member or friend of a user. For instance and without limitation, remote device 112 may be operated by an informed advisor such as user's functional medicine doctor who may generate a longevity inquiry 108 to determine the best form of Vitamin C for the user to consume and supplement user's diet with due to a recent diagnosis of adrenal fatigue. Longevity inquiry 108 may be transmitted from a remote device 112 to computing device 104 utilizing any network methodology as described herein.

With continued reference to FIG. 1, computing device 104 may include a graphical user interface 116. Graphical user interface 116 may include without limitation a form or other graphical element having data entry fields, wherein a user may select one or more fields to enter one or more longevity inquires. Graphical user interface 116 may provide a drop-down menu where a user may select a particular longevity element. For instance and without limitation, graphical user interface 116 may provide a drop-down menu of particular categories of longevity elements that a user may select from such as multi-vitamins, bone health, joint health, vision health, heart health, women's health, men's health, gastrointestinal health, healthy blood glucose, immune health, neurological health, stress management, metabolic detoxification, sports nutrition, children's health and the like. In an embodiment, a user may select a category of longevity elements such as heart health and generate a longevity inquiry 108 based on the selected category. Graphical user interface 116 may display one or more photographs of one or more longevity elements that a user may select and generate a longevity inquiry 108 to determine if the user should consume the selected longevity element or if the particular selected longevity element is compatible with user's body. Graphical user interface 116 may provide free form textual entry fields where a user may enter one or more longevity inquiries. For example, a user may type into a free form textual entry field an inquiry regarding a longevity element. Graphical user interface 116 may also be utilized to display one or more outputs to a user such as a tolerant longevity element as described in more detail below.

With continued reference to FIG. 1, computing device 104 is configured to receive at an image device 120 located on computing device 104 a wireless transmission from a remote device 112 containing a photograph of a longevity element. An "image device 120" as used in this disclosure, includes any device suitable to take a picture and/or photograph of a longevity element. Image device 120 may include for example, a camera, mobile phone camera, scanner, or the like. Image device 120 may be located on remote device 112. For example, a user may take a photograph of a longevity element using a camera located on remote device 112 such as a mobile phone camera. Image device 120 may be utilized to receive a photograph and/or picture of a longevity element that contains a unique identifier of the longevity element. A unique identifier may include a specific sequence of characters, numbers, letters, and/or words that may identify a particular longevity element. A unique identifier may include a globally recognized uniform identifier such as a uniform code commission (UCC) barcode. For example, a user may utilize a camera located on remote device 112 to take a picture of a UCC barcode located on a longevity element while user is at a health food store and submit a longevity inquiry 108 to determine if the user should purchase the longevity element and if the longevity element is compatible with the user's body.

With continued reference to FIG. 1, computing device 104 is configured to retrieve a biological extraction from a user database. A "biological extraction 124" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC) or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface 116 object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors.

With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides vulgates'*, *Bacteroides-Prevotella*, *Barnesiella* species, *Bifidobacterium longarm*, *Bifidobacterium* species, *Butyrivbrio crossotus*, *Clostridium* species, *Collinsella aerofaciens*, fecal color, fecal consistency, *Coprococcus eutactus*, *Desulfovibrio piger*, *Escherichia coli*, *Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, one or more biological extraction 124 may be stored in user database 128. User database 128 may be implemented, without limitation, as a relational database, a key-value retrieval datastore such as a NOSQL database, or any other form or structure for use as a datastore that a person skilled in the art would recognize as suitable upon review of the entirety of this disclosure.

With continued reference to FIG. 1, system 100 is configured to identify a first longevity element 132 associated with a user as a function of a longevity inquiry 108 and a biological extraction 124. A first longevity element 132 includes any supplement which includes any product intended to supplement the diet of a human being and/or animal. A supplement includes any of the supplements as described above. In an embodiment, one or more longevity element 132 may be contained within a longevity inquiry 108. For instance and without limitation, a first longevity inquiry 108 may include a particular mentioned and/or selected supplement such as when a user may select a supplement from a drop down menu on graphical user interface 116. Computing device 104 may include a language processing module 136 that may be configured to extract one or more words from a longevity inquiry 108 and identify one or more longevity element 132. Language processing module 136 may include any hardware and/or software module. Language processing module 136 may be configured to extract, from one or more inputs, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for ise as a Markov chain or Hidden Markov Model.

With continued reference to FIG. 1, language processing module 136 may operate to produce a language processing model. Language processing model may include a program automatically generated by a computing device 104 and/or language processing module 136 to produce associations between one or more words extracted from at least a document and detect associations, including without limitation mathematical associations, between such words, and/or associations of extracted words with categories of longevity inquiries, and/or categories of longevity element 132. Associations between language elements, where language elements include for purposes herein extracted words describing and/or including constitutional data and/or ameliorative recommendation data may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of a longevity inquiry 108, and/or a given category of longevity element 132. As a further example, statistical correlations and/or mathematical associations may include probabilistic formulas or relationships indicating a positive and/or negative association between at least an extracted word and/or a given element of constitutional data and/or ameliorative recommendation data; positive or negative indication may include an indication that a given document is or is not indicating a longevity element 132. For instance, and without limitation, a negative indication may be determined from a phrase such as "Vitamin D supplementation was not found to decrease fracture risk," whereas a positive indication may be determined from a phrase such as "fish oil was found to positively impact cardiovascular health," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on a computing device 104, or the like.

Still referring to FIG. 1, language processing module 136 and/or a computing device 104 may generate a language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of a longevity inquiry 108 and a given relationship of such categories to longevity element 132. There may be a finite number of categories of longevity inquires a given relationship and/or a given category of longevity element 132 to which an extracted word may pertain; an HMM inference algorithm, such as the forward-backward algorithm or the Viterbi algorithm, may be used to estimate the most likely discrete state given a word or sequence of words. Language processing module 136 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 136 may use a corpus of documents to generate associations between language elements in a language processing module 136, and a computing device 104 may then use such associations to analyze words extracted from one or more documents and determine that the one or more documents indicate significance of a category of a longevity inquiry 108 and a given relationship of such categories to longevity element 132. In an embodiment, a computing device 104 may perform this analysis using a selected set of significant documents, such as documents identified by one or more experts as representing good science, good clinical analysis, or the like; experts may identify or enter such documents via a graphical user interface 116 as described below, or may communicate identities of significant documents according to any other suitable method of electronic communication, or by providing such identity to other persons who may enter such identifications into a computing device 104. Documents may be entered into a computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, a computing device 104 may automatically obtain the document using such an identifier, for instance by submitting a request to a database or compendium of documents such as JSTOR as provided by Ithaka Harbors, Inc. of New York.

With continued reference to FIG. 1, computing device 104 may identify a first longevity element 132 associated with a user by receiving dietary training data 140 wherein dietary training data 140 includes a plurality of biological extraction 124 and a plurality of correlated longevity element 132. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be ADME applicable for two or more distinct machine-learning algorithms as described in further detail below. Training data used by computing device 104 may correlate any input data as described in this disclosure to any output data as described in this disclosure.

With continued reference to FIG. 1, "dietary training data 140" as used in this disclosure, includes a plurality of data entries each data entry containing biological extraction 124 and correlated longevity element 132. Dietary training data 140 and/or elements thereof may be entered by one or more users including for example by one or more experts from remote device 112 and/or from graphical user interface 116. Experts may include one or more physicians, medical experts, nurses, experts in a particular topic and the like who may hold one or more credentials that may certify them as an expert. Credentials may include one or more licenses such as a medical license or a license to practice in a particular field of medicine such as a license to prescribe controlled substances. Credentials may include one or more board certifications such as aa certified personal trainer, a certified group exercise instructor, a certified board expert in gastroenterology, a certified medical exercise specialist, a certification from an organization relating to functional medicine such as the American Academy of Anti-Aging Medicine and the like. Credentials may include a particular field of experience and practice such as a functional medicines physician, a rheumatologist, psychiatrist, and the like. Credentials may include publications in top leading medical journals, newspapers, and articles. Credentials may include participation in one or more clinical trials.

With continued reference to FIG. 1, computing device 104 is configured to generate using a first machine learning algorithm a dietary model 144 correlating biological extraction 124 with longevity element 132. Dietary model 144 may be generated using one or more machine learning processes. A machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithm defined as processes whereby a computing device 104 derives, from training data, a model for sorting inputs into categories or bins of data. Classification may be performed using, without limitation, linear classifiers such as without limitation logistic regression and/or naïve Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

Continuing to refer to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, computing device 104 generates using a first machine-learning algorithm a dietary model 144 correlating biological extraction 124 with longevity element 132. First machine-learning algorithm may include any of the machine-learning algorithms as described above. Computing device 104 receives a user biological extraction 124 which may include any of the biological extraction 124 as described above. Computing device 104 outputs a longevity element 132 using the first machine-learning algorithm. In an embodiment, computing device 104 may generate using a supervised machine-learning algorithm dietary model 144 correlating biological extraction 124 with longevity element 132 and utilizing dietary training data 140. Computing device 104 may receive a user biological extraction 124 such as for example, a blood sample analyzed for one or more intracellular and extracellular nutrient levels. Computing device 104 may utilize the biological extraction 124 containing the blood sample in combination with a supervised machine-learning algorithm and dietary training data 140 to generate dietary model 144 and output a longevity element 132. Longevity element 132 may include one or more supplements that may be selected for the user.

With continued reference to FIG. 1, computing device 104 is configured to select an ADME model 148 as a function of a biological extraction 124. An "ADME model," as used in this disclosure, includes any machine learning model including any mathematical representation of a relationship between inputs that include a longevity element 132 associated with a user and outputs that include an ADME factor 152. An "ADME factor 152" as used in this disclosure, includes one or more elements of data describing absorption, distribution, metabolism, and/or excretion of one or more longevity element 132. ADME factor 152 may describe the absorption, distribution, metabolism and/or excretion of one particular longevity element 132 such as a specific brand of Vitamin C. ADME factor 152 may describe the absorption, distribution, metabolism and/or excretion of a generic category of longevity element 132 such as Vitamin C which could include multiple different brands of Vitamin C. ADME factor 152 may describe the absorption, distribution, metabolism, and/or excretion of a category of longevity element 132 such as joint support longevity element 132 or vision support longevity element 132. Absorption may include the ability of a longevity element 132 to reach a tissue such as via mucous surfaces such as intestinal absorption in the digestive tract. Absorption may be altered by factors such as poor solubility of a longevity element 132. For example, vitamin B12 such as methylcobalamin contains very poor oral absorption and solubility, and as such is preferably administered as a sublingual tablet, as a nasal spray or as an injection. Absorption may also be altered by other factors such as gastric emptying time which can be affected by medical conditions such as diabetes that can cause gastroparesis and delayed gastrointestinal emptying time. Absorption may be altered by chemical instability of a longevity element 132 in the stomach, and the inability of a longevity element 132 to permeate the intestinal wall thereby reducing the extent to which a longevity element 132 is absorbed. Absorption may also affect bioavailability of a longevity element 132 as longevity element 132 that are poorly absorbed may have very little bioavailability and as such may need to be administered in an alternative dosage form. Distribution may include the ability of a longevity element 132 to be carried to its effector site, such as through the bloodstream. After passage through the bloodstream, a longevity element 132 may be distributed to one or more muscles and organs. The ability of a longevity element 132 to be distributed to one or more locations in the body may be affected by factors such as regional blood flow rates, molecular size, polarity and binding to serum proteins, and forming a complex. For example, a longevity element 132 such as levocarnitine is unable to be distributed across the blood brain barrier and as such acts systemically in the body outside of the blood brain barrier, while acetyl-l-carnitine is able to be distributed across the blood brain barrier and is effectively utilized for neurological conditions including memory issues and tremors seen in individuals with Parkinson's disease. Metabolism includes the ability of a longevity element 132 to be broken down as it enters the body. Metabolism may be carried out by the liver through redox enzymes or cytochrome P450 enzymes. As a longevity element 132 is metabolized, it may be converted to one or more new compounds known as metabolites. Excretion includes the ability of a longevity element 132 and its metabolites to be removed from the body via excretion such as through the kidneys and eventually into urine and/or in the feces. Excretion can occur at the kidneys where a longevity element 132 is excreted into urine. Excretion can occur in biliary tract where excretion begins in the liver and passes through to the gut until the longevity element 132 is excreted in urine or fecal elimination. Excretion can occur through the lungs such as by exhaling a longevity element 132 or its metabolites.

With continued reference to FIG. 1, computing device 104 may select an ADME model 148 from model database 156. Model database 156 may include any data structure suitable for use as user database 128 as described above. Computing device 104 may select an ADME model 148 by first identifying a genetic marker 160 contained within a biological extraction 124. A "genetic marker 160" as used in this disclosure, is a gene, deoxyribonucleic acid (DNA) sequence, and/or ribonucleic acid (RNA) sequence that may be utilized to identify individuals and/or species. A genetic marker 160 may include a variation such as a DNA sequence that contains a single base-pair change such as a single nucleotide polymorphism (SNP). A genetic marker 160 may include a variation such as a minisatellite where a certain DNA motif which may range in length from between 10 to 60 based pairs may be repeated 5-50 times. A genetic marker 160 may include a biochemical marker which may be utilized to detect variation at a gene product level such as a change in proteins or amino acids. A genetic marker 160 may include a molecular marker which may detect a variation of a nucleotide change such as a deletion, duplication, inversion, and/or insertion. A genetic marker 160 may include a genotype which may include a set of one or more genes. A genetic marker 160 may include a phenotype which may include one or more observable characteristics of an individual resulting from the interaction of its genotype with the environment. A genetic marker 160 may include one or more markers of cytochrome p450 enzymes such as one or more phenotypes that may be involved in the metabolism of one or more longevity element 132. For example, a genetic marker 160 such as a CYP2C9*2 phenotype may be associated with reduced enzymatic activity and thus reduced metabolism of a longevity element 132 metabolized through the CYP2C9 pathway. In yet another non-limiting example, a genetic marker 160 such as a CYP2D6*2A phenotype may be associated with rapid enzymatic activity and thus increased metabolism of a longevity element 132 metabolized through the CYP2D6 pathway. A genetic marker 160 may include any of the genetic body measurements as described above. For instance and without limitation, a genetic marker 160 may include an A/G genotype of the CYP17A1 gene responsible for producing an enzyme responsible for converting progesterone into androgens. An A/G genotype indicates a fast conversion thus indicating estrogen dominance while an A/A genotype indicates normal conditions.

With continued reference to FIG. 1, computing device 104 generates using genetic training data 164 and using a classification algorithm, a genetic classifier 168, wherein the genetic classifier 168 inputs a genetic marker 160 and outputs an ADME model 148. "Genetic training data 164" as used in this disclosure, includes a plurality of data entries, each data entry containing genetic marker 160 and correlated ADME model 148. Computing device 104 may generate genetic classifier 168 using a classification algorithm 172, defined as a process whereby a computing device 104 derives, from training data, a model known as a "classifier" for sorting inputs into categories or bins of data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, computing device 104 may be configured to generate genetic classifier 168 using a Naïve Bayes classification algorithm 172. Naïve Bayes classification algorithm 172 generates classifiers by assigning class labels to problem instances, represented as vectors of element values. Class labels are drawn from a finite set. Naïve Bayes classification algorithm 172 may include generating a family of algorithms that assume that the value of a particular element is independent of the value of any other element, given a class variable. Naïve Bayes classification algorithm 172 may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm 172 may include a gaussian model that follows a normal distribution. Naïve Bayes classification algorithm 172 may include a multinomial model that is used for discrete counts. Naïve Bayes classification algorithm 172 may include a Bernoulli model that may be utilized when vectors are binary.

With continued reference to FIG. 1, computing device 104 may be configured to generate genetic classifier 168 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of genetic marker 160, to clusters representing ADME model 148.

With continued reference to FIG. 1, genetic classifier 168 may be customized to a particular user. For instance and without limitation, genetic classifier 168 may receive genetic training data 164 as described which may be modified and/or updated matching identified genetic marker 160 and/or previously selected ADME model 148. For instance and without limitation, if a user has a particular genetic marker 160 such as a single nucleotide polymorphism (SNP) of a beta-globin gene resulting in glutamic acid being substituted by valine at position 6, thereby resulting in sickle cell anemia. In such an instance, a particular ADME model 148 may be selected as a result of the SNP. In such an instance, genetic classifier 168 may learn the particular ADME model 148 selected as a result of the SNP and may select the same ADME model 148 at a later point in time when presented with the same SNP for the same user. In yet another non-limiting example, genetic training data 164 may be updated resulting in a correlation between the above mentioned SNP of the beta-globin gene to select a different ADME model 148 that more closely hews to the SNP. In such an instance, genetic classifier 168 may select this ADME model 148 that more closely hews to the SNP as a result of learning this updated association received through updated genetic training data 164.

With continued reference to FIG. 1, computing device 104 selects an ADME model 148 as a function of generating a genetic classifier 168. Genetic classifier 168 may output an ADME model 148 utilizing a genetic marker 160 contained within a biological extraction 124. Computing device 104 may select an ADME model 148 by retrieving a biological extraction 124 from user database 128 wherein the biological extraction 124 includes a genetic marker 160 containing an ADME marker. An "ADME marker" as used in this disclosure, includes any indication as to the ADME profile of the biological extraction 124. Computing device 104 may label a genetic marker 160 with an ADME marker retrieved from a database such as from model database 156. For instance and without limitation, a genetic marker 160 such as an A/G genotype of the MCM6 gene that controls production of the lactase enzyme may contain an ADME marker that indicates a SNP of the MCM6 gene. In yet another non-limiting example, a genetic marker 160 that contains a substitution of a base such as purine for cytosine may contain an ADME marker that indicates a substitution mutation of the particular gene that is affected. Computing device 104 may utilize a biological extraction 124 containing an ADME marker to locate an ADME model 148 containing the ADME marker. For instance and without limitation, computing device 104 may locate an ADME model 148 within model database 156 containing an ADME marker that matches the ADME marker contained within a biological extraction 124.

With continued reference to FIG. 1, computing device 104 generates a machine-learning algorithm 176 utilizing an ADME model 148 that inputs a longevity element 132 associated with the user as an input and outputs an ADME factor 152. Machine-learning algorithm 176 includes any of the machine-learning algorithm 176 as described above. An ADME factor 152 includes any of the ADME factor 152 as described above, including one or more elements of data describing absorption, distribution, metabolism, and/or excretion of one or more longevity element 132. For instance and without limitation, an ADME factor 152 may include a description that a particular brand of immediate release turmeric will be poorly absorbed by a user due to an altered gastrointestinal microbiome, but a particular brand of slow release turmeric will have greater bioavailability and demonstrate a better rate of absorption. In yet another non-limiting example, an ADME factor 152 may indicate that a user who has impaired renal function may be better suited consuming a longevity element 132 that is metabolized hepatically as compared to a longevity element 132 that is metabolized renally. In yet another non-limiting example, a longevity element 132 may indicate that a particular genetic mutation such as a SNP that the user has may alter metabolism of a longevity element 132 when administered as a liquid or capsule, but that metabolism will not be affected if the longevity element 132 is applied as a transdermal cream.

With continued reference to FIG. 1, computing device 104 identifies a second longevity element 132 with the ADME factor 152 as a function of the first longevity element 132. For instance and without limitation, a longevity element 132 such as zinc may cause computing device 104 to identify a second longevity element 132 such as copper administered in conjunction with zinc based on the ADME factor 152 for zinc. In yet another non-limiting example, a first longevity element 132 such as chaste tree berry may cause computing device 104 to identify a second longevity element 132 such as diindolylmethane administered in conjunction with chaste tree berry based on the ADME factor for chaste tree berry. Computing device 104 may generate a second ADME factor 152 for a second longevity element 132 and identify a second tolerant longevity element 180 as a function of the second ADME factor 152. For example, computing device 104 may identify a second longevity element 132 such as Vitamin C administered in conjunction with a first longevity element 132 such as iron. Computing device 104 generates a second ADME factor 152 for the Vitamin C, and identifies a second tolerant longevity element 180 utilizing the second ADME factor 152 for the Vitamin C. Once the second longevity element is identified, the computing device may be configured to display the second longevity device to the user.

Alternatively or additionally, computing device 104 may be further configured to identify the second longevity element 132 compatible with the ADME factor 152 as a function of the first longevity device by identifying a first active ingredient contained in the first longevity element 132 and identifying a second longevity element 132 containing a second active ingredient, where the first active ingredient relates to the second active ingredient. An "active ingredient" as used in this disclosure, includes one or more ingredients present in a longevity element 132 that are biologically active. An active ingredient may also be referred to as an active substance. For instance and without limitation, computing device 104 may identify a first tolerant longevity element 180 such as a multivitamin containing a first active ingredient such as Vitamin B12 and a second tolerant longevity element 180 such as a B-complex containing a second active ingredient that includes Vitamin B12. A first active ingredient relating to a second active ingredient includes any duplication of active ingredients, contraindication of active ingredients, and/or excess supplementation of ingredients. A duplication of active ingredients may occur when a first active ingredient is the same as a second active ingredient. For instance and without limitation, a first active ingredient may include Vitamin D3 and a second active ingredient may include Vitamin D3. A contraindication of active ingredients may occur when a first active ingredient should not be consumed in combination with a second active ingredient. For instance and without limitation, a first active ingredient may include calcium and a second active ingredient may include iron. An excess supplementation of ingredients may occur when consumption of a first active ingredient in combination with a second active ingredient may cause an excess dose or quantity of ingredients. For instance and without limitation, a first active ingredient may include a multivitamin containing various b-vitamins and a second active ingredient may include a b-complex which may contain various other b-vitamins not contained within the multivitamin but when given in combination may cause an overdose of total b-vitamins. The computing device may further eliminate the first longevity element.

With continued reference to FIG. 1, computing device 104 is further configured to display the second longevity element to the user. A user may include any human being. A user may be a family member or an informed advisor of a user. The second longevity device may be displayed in any image device 120 which may be located in remote device 112. The image device 120 where the second longevity device may be displayed may include, but not limited to, a mobile phone, a computer monitor, or the like The second longevity element may be displayed as a photograph, an image, or the like. The second longevity element may be displayed as a digital communication which may include but not limited to an email message, a text message, or the like. The second longevity element may be displayed as an Uniform Resource Locator ("URL") address, a hyperlink, or the like. In a non-limiting examples, as diabetic user who is also asthmatic may need to take prednisone to control the asthma. A first longevity element 132 such as Prednisone may cause computing device 104 to identify a second longevity element 132 such as Albuterol based on the ADME factor for Prednisone. Albuterol may be displayed in the user's mobile device.

With continued reference to FIG. 1, computing device 104 selects the second longevity element as a tolerant longevity elements. A "tolerant longevity element 180" as used in this disclosure, includes any longevity element 132 that is compatible with a selected user. Compatibility includes any longevity element 132 that contributes to achieving and/or maintaining vibrant health and longevity, and which does not deter and result in an incompatibility with a user. For instance and without limitation, a longevity element 132 such as a particular brand of fish oil that is poorly absorbed and that does not penetrate into the gastrointestinal tract of a user may be incompatible and as such would not be deemed to be a tolerant longevity element 180. In such an instance, the particular brand of fish oil may appear to be well absorbed and well metabolized by a second user and as such may be considered a tolerant longevity element 180 for the second user. Selecting a tolerant longevity element 180 may include selecting the second longevity element 180 that is compatible with an ADME factor 152 as the tolerant longevity element. In an embodiment, the computing device 104 may be further configured to select the second longevity element compatible with the ADME factor, and selecting the second longevity element as a tolerant longevity element as a function of identification. For instance and without limitation, an ADME factor 152 may indicate that a user has impaired functioning mucous cells for a supplement of a first longevity element However, ADME factor 152 may indicate that a different supplement with an ADME factor 152 that is compatible with the ADME factor 152 may be absorbed. As such, a second longevity element 132 may be selected as the tolerant longevity element.

With continued reference to FIG. 1, identifying a tolerant longevity element 180 includes identifying a second longevity element 132 contraindicated with an identified tolerant longevity element 180 and eliminating the second longevity element 132 as a tolerant longevity element 180. For instance and without limitation, an identified second longevity element 132 such as valerian root may be identified as being contraindicated with an identified tolerant longevity element 180 such as St. John's wort and as such computing device 104 may eliminate valerian root as a tolerant longevity element 180. In yet another non-limiting example, an identified second longevity element 132 such as calcium may be identified as being contraindicated with an identified tolerant longevity element 180 such as magnesium and as such computing device 104 may eliminate calcium as a tolerant longevity element 180.

Figure 2:
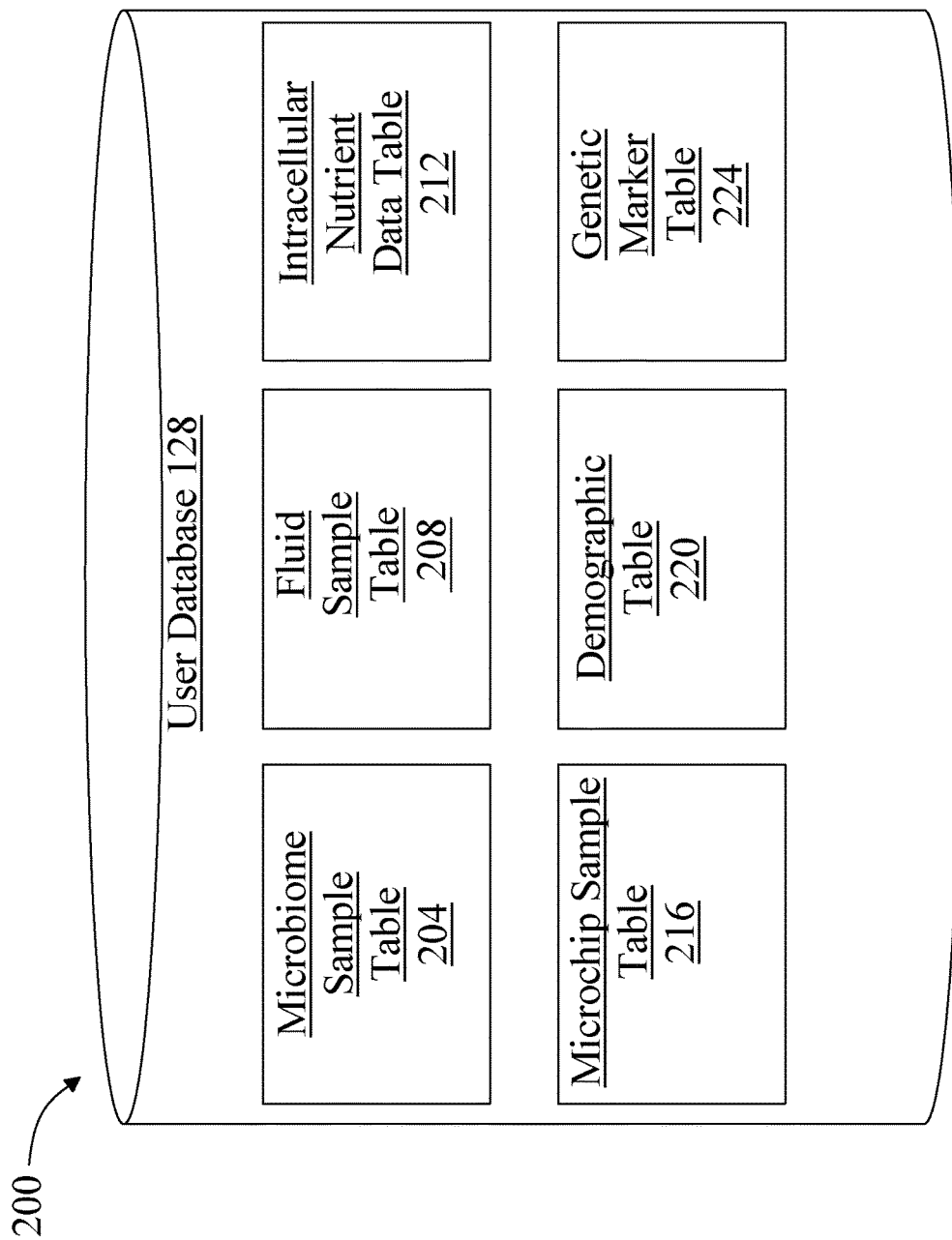
FIG. 2 is a block diagram illustrating an exemplary embodiment of a user database.

Referring now to FIG. 2, an exemplary embodiment 200 of user database 128 is illustrated. User database 128 may be implemented as any data structure as described above in reference to FIG. 1. One or more tables contained within user database 128 may include microbiome sample table 204; microbiome sample table 204 may include one or more biological extraction 124 relating to the microbiome. For instance and without limitation, microbiome sample table 204 may include a physically extracted sample such as a stool sample analyzed for the presence of pathogenic species such as parasites and anaerobes. One or more tables contained within user database 128 may include fluid sample table 208; fluid sample table 208 may include one or more biological extraction 124 containing fluid samples. For instance and without limitation, fluid sample table 208 may include a urine sample analyzed for the presence or absence of glucose. One or more tables contained within user database 128 may include intracellular nutrient data table 212; intracellular nutrient data table 212 may include one or more biological extraction 124 containing intracellular nutrient levels. For instance and without limitation, intracellular nutrient data table 212 may include a blood sample analyzed for intracellular levels of Vitamin B12. One or more tables contained within user database 128 may include microchip sample table 216; microchip sample table 216 may include one or more biological extraction 124 obtained from a microchip. For instance and without limitation, microchip sample table 216 may include a blood sugar level obtained from a microchip embedded under a user's skin. One or more tables contained within user database 128 may include demographic table 220; demographic table 220 may include one or more demographic inputs pertaining to a user. For instance and without limitation, demographic table 220 may include information pertaining to a user's full name, address, date of birth, sex, marital status, occupation, and the like. One or more tables contained within user database 128 may include genetic marker table 224; genetic marker table 224 may include one or more biological extraction 124 containing one or more genetic marker 160. For instance and without limitation, genetic marker table 224 may include a blood sample result analyzed for the genotype of the MCM6 gene of a user.

Figure 3:
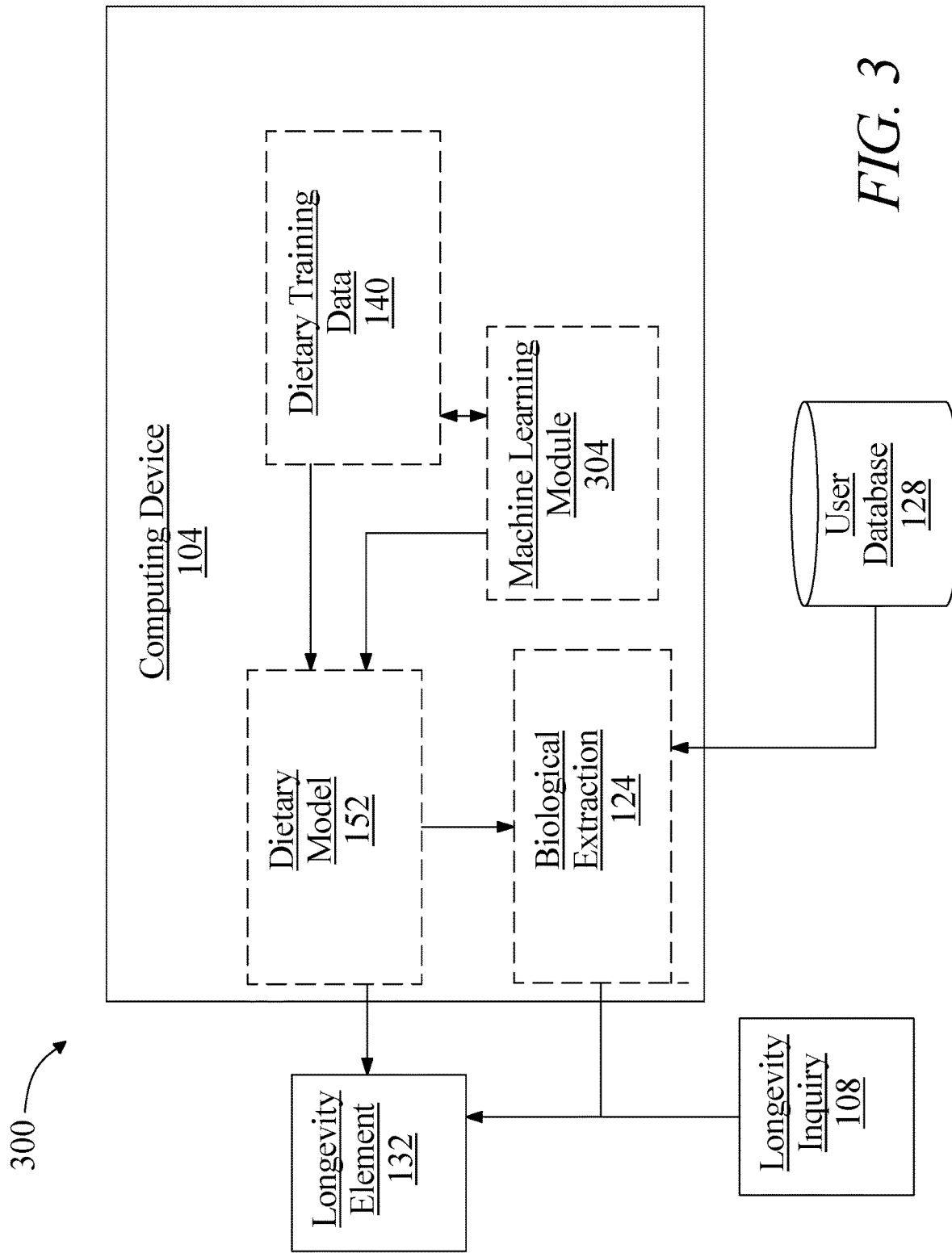
FIG. 3 is a diagrammatic representation of dietary model.

Referring now to FIG. 3, an exemplary embodiment 300 of dietary model 144 is illustrated. Computing device 104 identifies a longevity element 132 associated with a user by receiving dietary training data 140. Dietary training data 140 includes any of the dietary training data 140 as described above in reference to FIG. 1. Dietary training data 140 includes a plurality of biological extraction 124 and a plurality of correlated longevity element 132. For instance and without limitation, dietary training data 140 may include a biological extraction 124 such as a saliva sample containing one or more salivary hormone levels such as elevated estradiol and estrone levels correlated to one or more longevity element 132 such as calcium d-glucarate, milk thistle, dandelion root, and chaste tree berry. Computing device 104 may include machine-learning module 304. Machine-learning module may be implemented as any hardware and/or software module. Machine-learning module 304 may be configured to calculate one or more machine-learning algorithm 176. Machine-learning algorithm 176 include any of the machine-learning algorithm 176 as described above. For instance and without limitation, machine-learning module 304 may generate a supervised machine-learning algorithm 176 utilizing a user biological extraction 124 retrieved from user database 128 as an input and outputting a longevity element 132. Machine-learning module 304 may generate an unsupervised machine-learning algorithm 176 utilizing a user biological extraction 124 retrieved from user database 128 as an input and outputting a longevity element 132. Machine-learning module 304 may generate a lazy-learning algorithm utilizing a user biological extraction 124 retrieved from user database 128 as an input and outputting a longevity element 132. Machine-learning module 304 may generate one or more machine-learning algorithm 176 including a combination of one or more algorithms as described above. Machine-learning module 304 generates using a first machine-learning model dietary model 144 correlating biological extraction 124 with longevity element 132. Dietary model 144 may include any machine learning process and may include linear or polynomial regression algorithms. Dietary model 144 may include one or more equations. Dietary model 144 may include a set of instructions utilized to generate outputs based on inputs derived using a machine-learning algorithm 176 and the like. Dietary model 144 outputs a longevity element 132. Longevity element 132 includes any of the longevity element 132 as described above in reference to FIG. 1.

Figure 4:
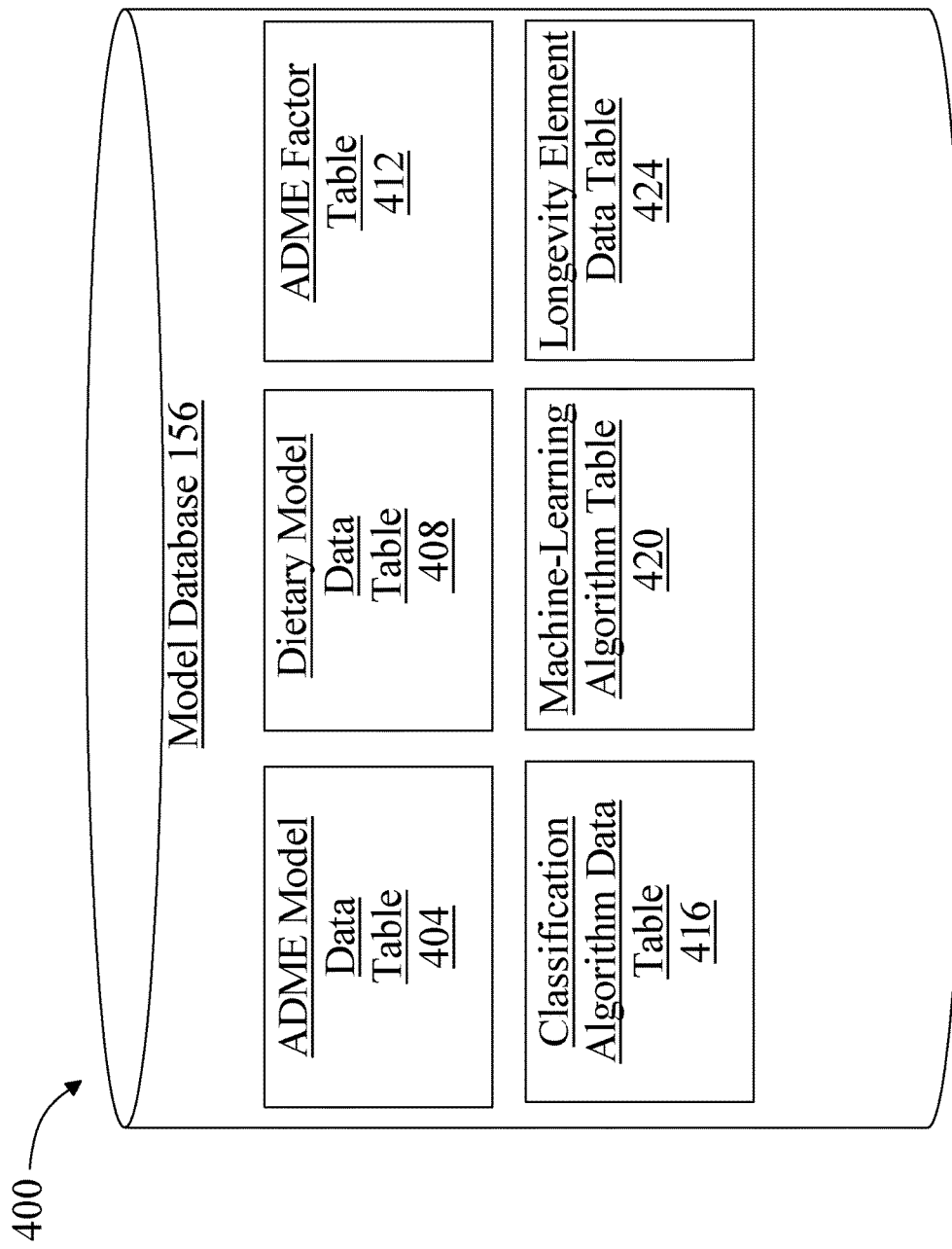
FIG. 4 is a block diagram illustrating an exemplary embodiment of a model database.

Referring now to FIG. 4, an exemplary embodiment 400 of model database 156 is illustrated. Model database 156 may be implemented as any data structure suitable for use as user database 128 as described above in more detail in reference to FIG. 1. One or more tables contained within model database 156 may include ADME model 148 data table 404; ADME model 148 data table 404 may include one or more data entries containing ADME model 148. One or more tables contained within model database 156 may include dietary model 144 data table 408; dietary model 144 data table may include one or more data entries containing one or more dietary model 144. One or more tables contained within model database 156 may include ADME factor 152 table 412; ADME factor 152 table 412 may include one or more data entries containing one or more ADME factor 152. One or more tables contained within model database 156 ADME include classification algorithm 172 data table 416; classification algorithm 172 data table 416 may include one or more data entries containing one or more classification algorithm 172. One or more tables contained within model database 156 may include machine-learning algorithm 176 table 420; machine-learning algorithm 176 table 420 may include one or more data entries containing one or more machine-learning algorithm 176. One or more tables contained within model database 156 may include longevity element 132 data table 424; longevity element 132 data table 424 may include one or more data entries containing one or more longevity element 132.

Figure 5:
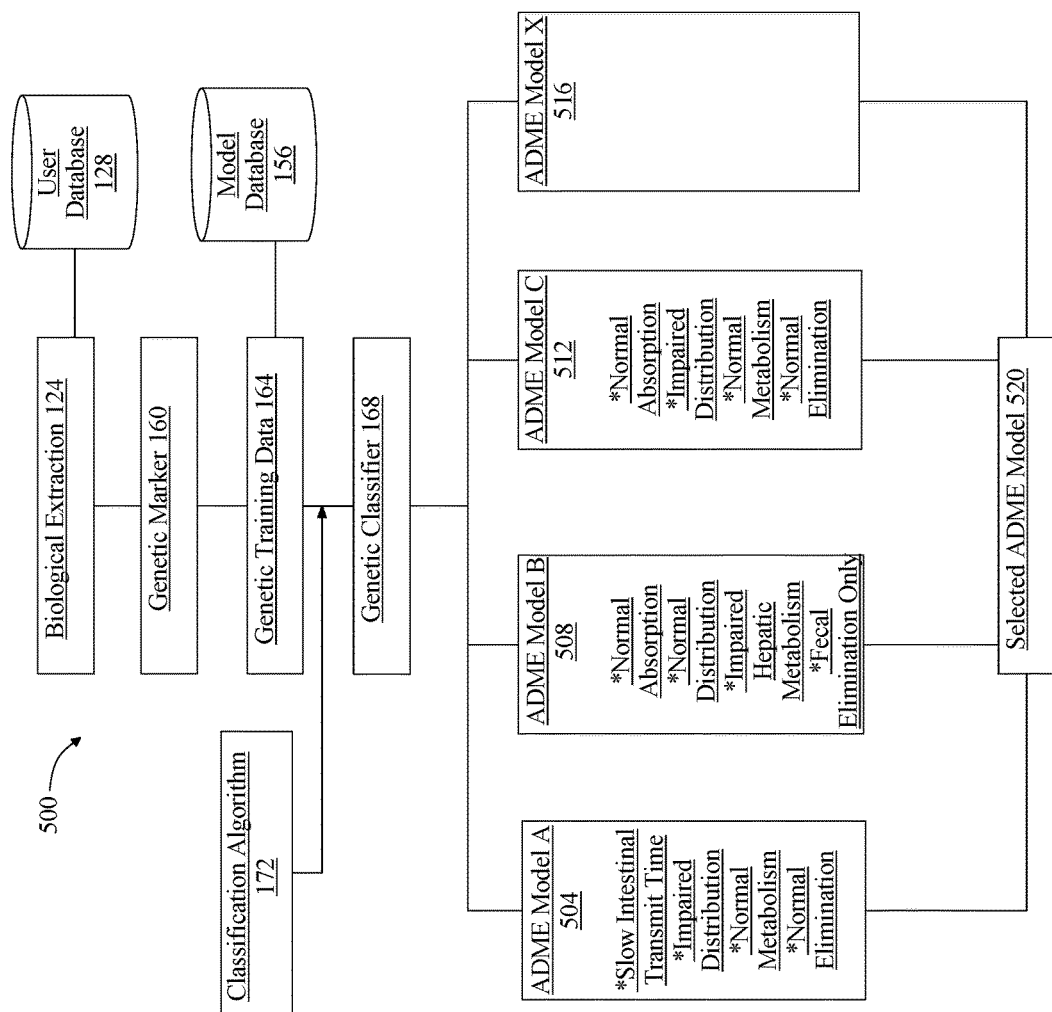
FIG. 5 is a diagrammatic representation of genetic classifier.

Referring now to FIG. 5, an exemplary embodiment of genetic classifier 168 is illustrated. Genetic classifier 168 may be generated by computing device 104 utilizing any of the methodologies as described above. Computing device 104 identifies a genetic marker 160 contained within a biological extraction 124. One or more biological extraction 124 may be stored in user database 128 as described above in more detail in reference to FIGS. 1-2. Genetic marker 160 includes any of the genetic marker 160 as described above in reference to FIG. 1. For instance and without limitation, genetic marker 160 may include a salivary sample analyzed for a user's genotype for the NOS3 gene responsible for controlling production of enzymes involved in regulating vaso-dilation and vaso-constriction. In yet another non-limiting example, genetic marker 160 may include a blood sample analyzed for a user's genotype for the SLCO1B1 gene responsible for directing influx efficiency of pharmaceuticals into cells. Computing device 104 generates using genetic training data 164 and using a classification algorithm 172 a genetic classifier 168. Genetic training data 164 includes any of the genetic training data 164 as described above. Genetic training data 164 includes a plurality of data entries containing genetic marker 160 and correlated ADME model 148. Classification algorithm 172 include any of the classification algorithm 172 as described above, including for example linear classifiers, fisher's linear discriminant, support vector machines, quadratic classifiers, kernel estimation, k-nearest neighbor, decision trees, random forests, neural networks, learning vector quantization and the like.

With continued reference to FIG. 5, computing device 104 selects an ADME model 148 as function of generating genetic classifier 168. In an embodiment, ADME model 148 A 504 may include a model that is best suited for a user with slow intestinal transit time, impaired distribution, normal metabolism, and normal elimination. In an embodiment, ADME model 148 B 508 may include a model that is best suited for a user with normal absorption, normal distribution, impaired hepatic metabolism, and fecal elimination only. In an embodiment, ADME model 148 C 512 may include a model that is best suited for a user with normal absorption, impaired distribution, normal metabolism, and normal elimination. Genetic classifier 168 may select an ADME model 148 from ADME model 148 X 516 or an indefinite number of ADME model 148. Selected ADME model 148 520 is utilized by computing device 104 to generate a machine-learning algorithm 176 utilizing the ADME model 148 that inputs a longevity element 132 associated with a user as an input and outputs an ADME factor 152.

Figure 6:
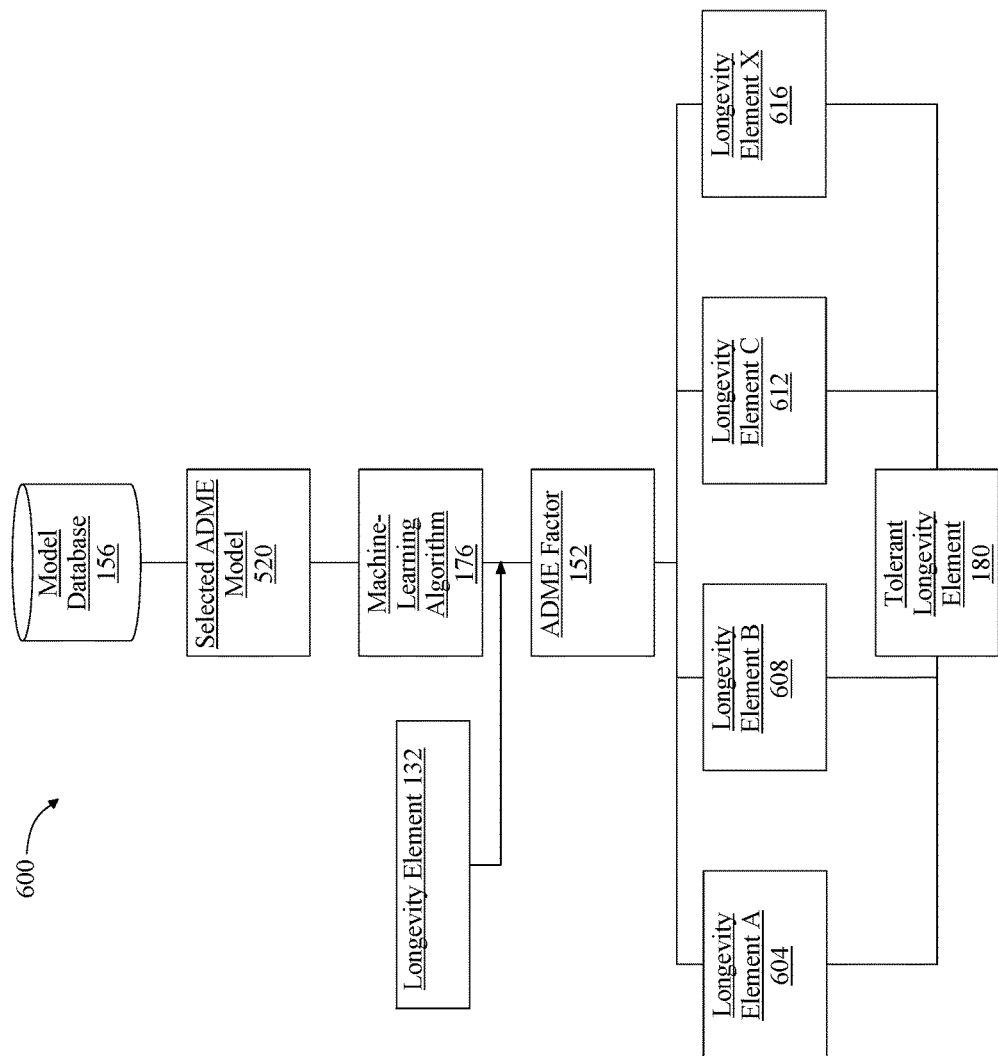
FIG. 6 is a diagrammatic representation of machine-learning algorithms.

Referring now to FIG. 6, an exemplary embodiment of machine-learning algorithm 176 is illustrated. Computing device 104 generates a machine-learning algorithm 176 utilizing the selected ADME model 148. Computing device 104 may retrieve the selected ADME model 148 from model database 156. ADME model 148 may be selected utilizing any of the methodologies as described herein. Computing device 104 generates a machine-learning algorithm 176, including any of the machine-learning algorithm 176 as described above. For instance and without limitation, computing device 104 may generate a machine-learning algorithm 176 such as a supervised machine-learning algorithm 176, an unsupervised machine-learning algorithm 176, linear regression, logistic regression, decision tree, naïve bayes, k-nearest neighbor-k-means clustering, random forest, and the like. Selected ADME model 148 utilizes a longevity element 132 associated with the user as an input and outputs an ADME factor 152. ADME factor 152 includes any of the ADME factor 152 as described above. For instance and without limitation, a longevity element 132 associated with the user may include a fish oil supplement. ADME factor 152 may be utilized to select one or more longevity element 132 containing various doses, dosage forms, flavors, and the like of fish oil. ADME factor 152 may be utilized to select between for example, longevity element 132 A 604 which may contain a liquid unflavored form of fish oil. ADME factor 152 may be utilized to select between for example, longevity element 132 B 608 which may include a liquid flavored fish oil containing orange sherbet flavor. ADME factor 152 may be utilized to select between for example, longevity element 132 C 612 which may include a capsule form of fish oil containing 500 mg in each capsule. ADME factor 152 may be utilized to select longevity element 132 X or an indefinite number of longevity element 132. Computing device 104 selects a tolerant longevity element 180 utilizing ADME factor 152 as described above in reference to FIG. 1.

Figure 7:
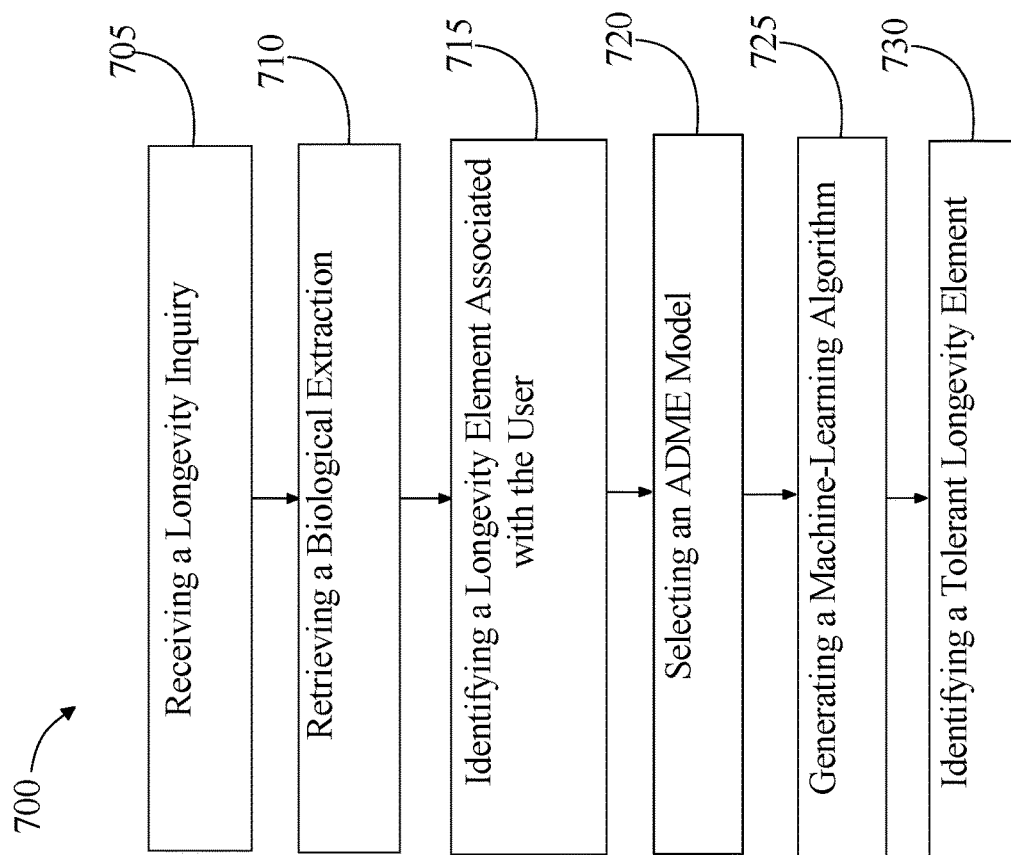
FIG. 7 is a process flow diagram illustrating an exemplary embodiment of a method of optimizing supplement decisions.

Referring now to FIG. 7, an exemplary embodiment of a method 700 of optimizing supplement decisions is illustrated. At step 705 a computing device 104 receives a longevity inquiry 108 from a remote device 112. Computing device 104 receives a longevity inquiry 108 utilizing any network methodology as described herein. Longevity inquiry 108 includes any of the longevity inquires as described above in reference to FIG. 1. For instance and without limitation, a longevity inquiry 108 may include a question regarding if a user should consume a particular supplement such as a ubiquinol supplement recommended by the user's friend. In yet another non-limiting example, a longevity inquiry 108 may include a description of a particular symptom that a user experiences such as a description of stabbing back pain upon waking and lifting anything over five pounds and an inquiry as to a supplement that a user can consume to reduce stabbing back pain. In yet another non-limiting example, a longevity inquiry 108 may include a selection of one or more supplements and/or supplement categories that may be displayed on graphical user interface 116 located on computing device 104. In an embodiment, computing device 104 may display a picture of one or more longevity element 132 that a user may select to determine if the user should consume the particularly selected longevity element 132. In an embodiment, a longevity inquiry 108 may be generated by a family member, friend, neighbor, spouse, boyfriend, girlfriend, informed advisor and the like inquiring as to if the user should consume a particular supplement, a description of one or more symptoms that the user may be experiencing and the like. For example, an informed advisor such as user's yoga teacher may generate a longevity inquiry 108 after a yoga class where user complains of stiff muscles, pain in user's neck, and low back spasm. In an embodiment, a longevity inquiry 108 may include a particular brand of supplement with an inquiry from a user seeking to know if the particular brand of supplement is compatible with the user's body. Computing device 104 receives a longevity inquiry 108 from a remote device 112, which may include any of the remote device 112 as described above in reference to FIG. 1.

With continued reference to FIG. 7, receiving a longevity inquiry 108 may include receiving a photograph of a longevity element 132. Computing device 104 may receive at an image device 120 located on computing device 104 a wireless transmission from remote device 112 containing a photograph of a longevity element 132. Longevity element 132 includes any of the longevity element 132 as described above in reference to FIGS. 1-6. Image device 120 includes any of the image device 120 as described above in reference to FIGS. 1-6. In an embodiment, a user may take a photograph of a particular longevity element 132 such as when user is shopping in a health food store with a camera located on user's mobile phone. In such an instance, image device 120 located on computing device 104 may receive the photograph of the longevity element 132. In an embodiment, a photograph of a longevity element 132 may include a photograph of a unique identifier of a longevity element 132 such as a universal product code (UPC) containing 12 numeric digits uniquely identifying a longevity element 132. Unique identifier may include an international article number of European article number (EAN).

With continued reference to FIG. 7, at step 710 a computing device 104 retrieves a biological extraction 124 from a user database 128. Biological extraction 124 includes any of the biological extraction 124 as described above in reference to FIG. 1. For instance and without limitation, a biological extraction 124 may include a stool sample analyzed for one or more markers of digestion and absorption such as chymotrypsin, putrefactive short-chain fatty acids, meat and vegetable fibers, and fecal fats. In yet another non-limiting example, a biological extraction 124 may include a hair sample analyzed for levels of one or more toxic elements such as lead, mercury, arsenic, bismuth, cesium, platinum, tin, and uranium. One or more biological extraction 124 may be stored in user database 128 which may include any data structure as described above in reference to FIGS. 1-2.

With continued reference to FIG. 7, at step 715 a computing device 104 identifies a longevity element 132 associated with a user as a function of a longevity inquiry 108 and a biological extraction 124. Longevity element 132 includes any of the longevity element 132 as described above in reference to FIGS. 1-6. In an embodiment, a longevity element 132 may be contained within a longevity inquiry 108 such as when a longevity inquiry 108 may name a particular supplement brand or category of supplement. For instance and without limitation, a longevity inquiry 108 may include a question as to the best multivitamin product that a user should consume. In yet another non-limiting example, a longevity inquiry 108 may include a description of a particular supplement brand such as 365 everyday Value Folic Acid as produced by WHOLE FOODS MARKET of Austin, Texas Computing device 104 may utilize language processing module 136 to extract one or more longevity element 132 contained within a longevity inquiry 108. This may be performed utilizing any of the methodologies as described above in reference to FIG. 1.

With continued reference to FIG. 7, identifying a longevity element 132 associated with a user may include generating a machine-learning algorithm 176. Computing device 104 may receive dietary training data 140. Dietary training data 140 may include any of the dietary training data 140 as described above in reference to FIG. 1. Dietary training data 140 may include a plurality of data entries including biological extraction 124 correlated to longevity element 132. Computing device 104 may receive dietary training data 140 from model database 156. Computing device 104 generates using a first machine-learning algorithm 176 a dietary model 144 correlating biological extraction 124 with longevity element 132. Dietary model 144 includes any of the dietary model 144 as described above. Dietary model 144 may include one or more equations. Dietary model 144 may include any machine-learning process and may include linear or polynomial regression algorithms. Dietary model 144 may include one or more supervised machine-learning algorithm 176. Dietary model 144 may include one or more unsupervised machine-learning algorithm 176. Dietary model 144 may include one or more lazy learning models. Dietary model 144 may include a set of instructions utilized to generate outputs based on inputs derived using one or more machine-learning algorithm 176. Computing device 104 receives a user biological extraction 124 and outputs a longevity element 132 using a first machine-learning algorithm 176. Longevity element 132 includes any of the longevity element 132 as described herein.

With continued reference to FIG. 7, at step 720 a computing device 104 selects an ADME model 148 as a function of a biological extraction 124. ADME model 148 includes any of the ADME model 148 as described above in reference to FIGS. 1-6. Computing device 104 may select an ADME model 148 utilizing any of the methodologies as described above. Computing device 104 may select an ADME model 148 by generating genetic classifier 168. Computing device 104 identifies a genetic marker 160 contained within a biological extraction 124. Genetic marker 160 includes any of the genetic marker 160 as described above in reference to FIGS. 1-6. For instance and without limitation, a biological extraction 124 such as a blood sample may contain a genetic marker 160 that includes a user T/T genotype of the MTHFR gene. In yet another non-limiting example, a biological extraction 124 such as a salivary sample may contain a genetic marker 160 that includes a user G/A genotype of the SHMT1 gene. Computing device 104 generates using genetic training data 164 including a plurality of genetic marker 160 and a plurality of correlated ADME model 148 and using a classification algorithm 172, genetic classifier 168. This may be performed utilizing any of the methods as described above in reference to FIGS. 1-6. Genetic classifier 168 inputs a genetic marker 160 and outputs an ADME model 148. For instance and without limitation, a genetic marker 160 such as a G/G genotype of the MTR gene indicating suboptimal production of enzymes involved in metabolism and utilization by the body of Vitamin B12 may be utilized by genetic classifier 168 in combination with generating a classification algorithm 172 and genetic training data 164 to select an ADME model 148 that contains impaired absorption, adequate distribution, impaired metabolism, and adequate elimination. Computing device 104 selects an ADME model 148 as a function of generating a genetic classifier 168. This may be performed utilizing any of the methodologies as described above in reference to FIGS. 1-6.

With continued reference to FIG. 7, selecting an ADME model 148 may include retrieving a biological extraction 124 from user database 128 wherein the biological extraction 124 includes a genetic marker 160 containing an ADME marker and locating an ADME model 148 containing the ADME marker. ADME marker includes any indication as to the ADME profile of the biological extraction 124. For instance and without limitation, a biological extraction 124 containing an A/A genotype of the MTR gene that controls metabolism of Vitamin B12 as described above may contain an ADME marker that labels the genetic marker 160 as optimal because the A/A genotype is the expected genotype assuming no SNPs or mutations. Similarly, a biological extraction 124 containing a G/G genotype of the MTR gene may contain an ADME marker that labels the genetic marker 160 as suboptimal because of the increased risk of elevated homocysteine and associated health risks such as increased risk for a myocardial infarction and heart disease seen in users with the G/G genotype but not the A/A genotype. Computing device 104 locates an ADME model 148 containing an ADME marker that matches the ADME marker contained on the biological extraction 124. Computing device 104 may retrieve one or more ADME model 148 from model database 156. Biological extraction 124 containing an ADME marker may be stored in user database 128.

With continued reference to FIG. 7, at step 725 a computing device 104 generates a machine-learning algorithm 176 utilizing an ADME model 148 that inputs a longevity element 132 associated with the user as an input and outputs an ADME factor 152. ADME model 148 includes any of the ADME model 148 as described above. ADME model 148 inputs a longevity element 132 associated with a user and outputs an ADME factor 152. ADME factor 152 includes one or more elements of data describing absorption, distribution, metabolism, and/or excretion of one or more longevity element 132. ADME factor 152 includes any of the ADME factor 152 as described above in reference to FIG. 1.

With continued reference to FIG. 7, at step 730 a computing device 104 identifies a tolerant longevity element 180 as a function of an ADME factor 152. Tolerant longevity element 180 includes any of the tolerant longevity element 180 as described above in reference to FIGS. 1-6. Identifying a tolerant longevity element 180 includes selecting a tolerant longevity element 180 compatible with an ADME factor 152. For instance and without limitation, an ADME factor 152 that indicates impaired gastrointestinal absorption may be utilized to select a tolerant longevity element 180 that does not require gastrointestinal absorption such as in an injectable dosage form or a suppository dosage form intended for rectal or vaginal administration. In yet another non-limiting example, an ADME factor 152 that indicates impaired hepatic elimination may be utilized to select a tolerant longevity element 180 that does not require hepatic elimination but rather is almost solely renally eliminated into urine. Identifying a tolerant longevity element 180 includes identifying by computing device 104 a second longevity element 132 administered in conjunction with an identified tolerant longevity element 180. For instance and without limitation, an identified tolerant longevity element 180 containing calcium carbonate may cause computing device 104 to identify Vitamin D which can be administered in conjunction with calcium carbonate. Computing device 104 generates a second ADME factor 152 for the Vitamin D, utilizing any of the methodologies as described above. Computing device 104 identifies a second tolerant longevity element 180 as a function of the second ADME factor 152. For example, computing device 104 may identify a particular brand of Vitamin D that user may tolerate and that may be administered in conjunction with calcium carbonate. In an embodiment, second ADME factor 152 may cause computing device 104 to not be able to identify a second tolerant longevity element 180. In such an instance, user may be instructed only to consume first tolerant longevity element 180.

With continued reference to FIG. 7, identifying a tolerant longevity element 180 includes identifying a second longevity element 132 contraindicated with an identified tolerant longevity element 180 and eliminating the second longevity element 132 as a tolerant longevity element 180. For instance and without limitation, computing device 104 may identify a tolerant longevity element 180 such as melatonin for a user with insomnia. Computing device 104 may identify a second longevity element 132 such as 5-hydroxytryptophan which may also be utilized for insomnia. Computing device 104 may eliminate 5-hydroxytryptophan as a possibly identified tolerant longevity element 180 due to the contraindication if a user were to consume both melatonin and 5-hydroxytryptophan causing excessive drowsiness, fatigue, and even respiratory depression. Identifying a tolerant longevity element 180 may include identifying by computing device 104 a first tolerant longevity element 180 containing a first active ingredient. Computing device 104 identifies a second tolerant longevity element 180 containing a second active ingredient. Computing device 104 determines that the first active ingredient relates to the second active ingredient and eliminates the second tolerant longevity element 180. For instance and without limitation, computing device 104 may identify a first tolerant longevity element 180 such as a multi-vitamin which may contain multiple first active ingredients such as Vitamin A, Vitamin C, iron, zinc, and copper. Computing device 104 may identify a second tolerant longevity element 180 such as an iron supplement, whereby computing device 104 may determine that iron contained within the second tolerant longevity element 180 relates to the iron contained within the first tolerant longevity element 180. In such an instance, computing device 104 may eliminate the second tolerant longevity element 180 upon determining that the dose of iron contained in the second tolerant longevity element 180 would be in excess of the daily recommended dose of iron when consumed in combination with the first tolerant longevity element 180. In an embodiment, a health professional such as an informed advisor may override this decision when they may deem that both products can be safely taken together such as for example if a user recently experienced a large volume of blood loss or was in a traumatic motor vehicle accident and lost excess amounts of blood.

Figure 8:
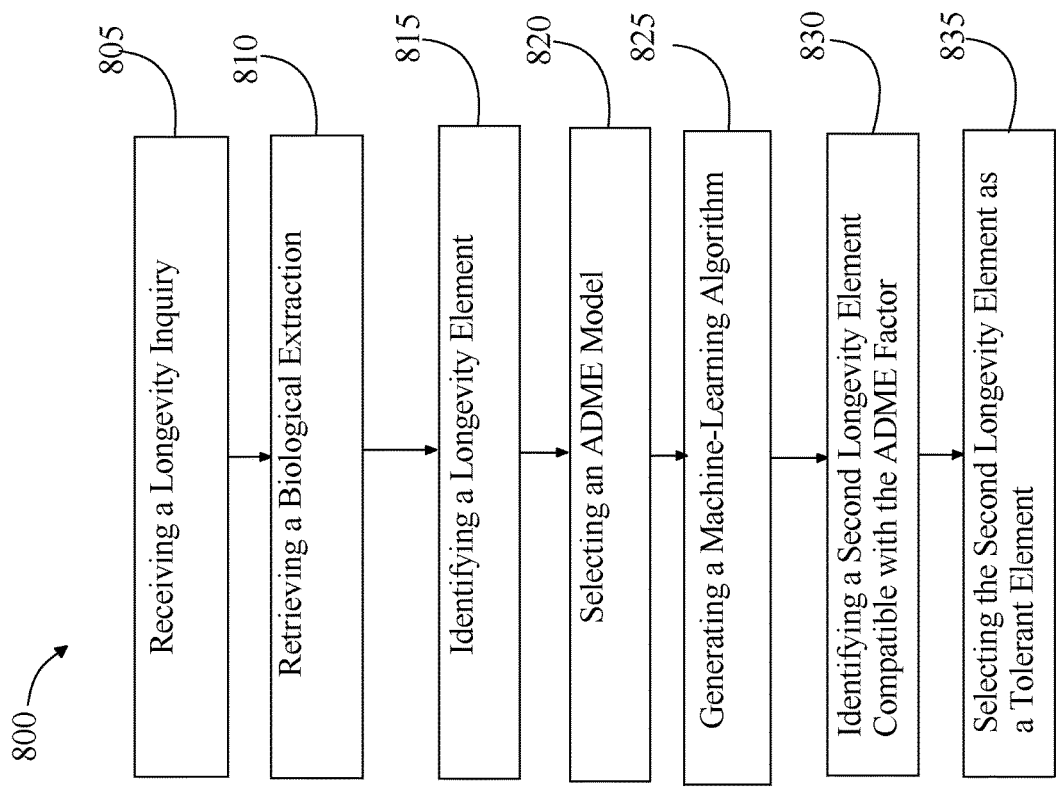
FIG. 8 is a process flow diagram illustrating an exemplary embodiment of a method of optimizing supplement decisions.

Referring now to FIG. 8, an exemplary embodiment of a method 800 of optimizing supplement decisions is illustrated. At step 805, a computing device receives a longevity inquiry from a remote device, the longevity query identifying a first longevity element; this may be implemented as described above, for instance by receiving a user identification of first longevity element. For instance, and without limitation, computing device may receive, at an image device located on the computing device, a transmission, such as a wireless transmission and/or a transmission over a network, from the remote device containing data describing first longevity element and/or a product containing first longevity element, such as without limitation a photograph of a longevity element, an optically captured and/or otherwise captured identifier from an NFC tag, RFID tag, bar code, and/or quick read (QR) code, and/or an identifier selected user interaction and/or network communication, such as a uniform resource locator (URL), uniform resource identifier (URI), stock-keeping unit (SKU) or the like. Alternatively or additionally, first longevity element and/or a product containing first longevity element may be identified as a user selection in an online shopping cart, a user selection on a website, and/or a user textual entry.

Alternatively or additionally, and still referring to FIG. 8, a longevity inquiry may be received by way of receipt of a user biological extraction; for instance, user may submit a new biological extraction and/or refer to a stored biological extraction while inquiring about longevity elements to aid user in overcoming or preventing chronic conditions and/or extending life-span. For instance, and as described above, computing device may receive dietary training data wherein dietary training data includes a plurality of biological extractions and a plurality of correlated longevity elements, and generate therewith a first machine learning algorithm a dietary model relating biological extractions to longevity elements; computing device may train first machine learning algorithm using training data. Computing device may receive a second biological extraction; second biological extraction may be the same biological extraction as a first biological extraction as described below, and/or may be a different biological extraction. Receipt of second biological extraction may be effected in any manner described above in reference to FIGS. 1-7. Computing device may output the first longevity element using the first machine learning algorithm and the second biological extraction; this may be accomplished without limitation as described above in reference to FIGS. 1-7. As a non-limiting example, first machine learning algorithm may include a supervised machine-learning algorithm. As a function of a longevity inquiry and a biological extraction, computing device identifies a longevity element.

With continued reference to FIG. 8, at step 815 a computing device identifies a longevity element associated with a user as a function of a longevity inquiry and a biological extraction. This may be implemented, without limitation, as described above in reference to FIGS. 1-7. In an embodiment, a computing device may identify the first longevity element associated with the user by receiving dietary training data wherein dietary training data includes a plurality of biological extractions and a plurality of correlated longevity element, receiving a second biological extraction, and outputs a first longevity element using the first machine learning algorithm. As a function of the biological extraction, computing device selects an ADME model.

At step 820, computing device selects an ADME model as a function of the first biological extraction; this may be implemented, without limitation, as described above in reference to FIGS. 1-7. Utilizing the selected ADME model, computing device generates a machine-learning algorithm.

At step 825, computing device generates a machine-learning algorithm utilizing selected ADME model that inputs first longevity element associated and outputs an ADME factor. In an embodiment, the first machine language may comprise a supervised machine-learning algorithm. In an embodiment, the computing device may select the ADME model by identifying a genetic marker contained within a third biological extraction; generating using genetic training data including a plurality of genetic markers and a plurality of correlated ADME models, and using a classification algorithm, a genetic classifier, wherein the genetic classifier inputs a genetic marker and outputs an ADME model; and selecting an ADME model as a function of generating the generic classifier. In an embodiment, the computing device may select an ADME model by retrieving a fourth biological extraction from the user database wherein the biological extraction further comprises a genetic marker containing an ADME marker and locating an ADME model containing the ADME marker. This may be implemented, without limitation, as described above in reference to FIGS. 1-7. From a compatible ADME factor, the computing device identifies a second longevity element.

At step 830, computing device identifies a second longevity element compatible with the ADME factor; this may be performed, without limitation, as described above in reference to FIGS. 1-7. For instance and without limitation, a longevity element such as zinc may cause computing device to identify a second longevity element such as copper administered in conjunction with zinc based on the ADME factor for zinc. In yet another non-limiting example, a first longevity element 132 such as chaste tree berry may cause computing device to identify a second longevity element such as diindolylmethane administered in conjunction with chaste tree berry based on the ADME factor for chaste tree berry. Computing device may identify a second longevity element compatible with the ADME factor as a function of the first longevity element by identifying a first active ingredient contained in the first tolerant longevity element. Computing device may identify a second longevity element containing a second active ingredient, where the first active ingredient relates to the first active ingredient. For instance and without limitation, a first active ingredient may include Vitamin D3 and a second active ingredient may include Vitamin D3. A contraindication of active ingredients may occur when a first active ingredient should not be consumed in combination with a second active ingredient. For instance and without limitation, a first active ingredient may include calcium and a second active ingredient may include iron. An excess supplementation of ingredients may occur when consumption of a first active ingredient in combination with a second active ingredient may cause an excess dose or quantity of ingredients. For instance and without limitation, a first active ingredient may include a multivitamin containing various b-vitamins and a second active ingredient may include a b-complex which may contain various other b-vitamins not contained within the multivitamin but when given in combination may cause an overdose of total b-vitamins. The computing device may eliminate the first longevity element. A second longevity element is selected as a tolerant longevity element.

At step 835, computing device selects the second longevity element as a tolerant longevity element. the computing device may select a tolerant longevity element by identifying a second longevity element compatible with the ADME factor; and selecting the second longevity element as a tolerant longevity element. For instance and without limitation, a longevity element such as a particular brand of fish oil that is poorly absorbed and that does not penetrate into the gastrointestinal tract of a user may be incompatible and as such would not be deemed to be a tolerant longevity element. In such an instance, the particular brand of fish oil may appear to be well absorbed and well metabolized by a second user and as such may be considered a tolerant longevity element for the second user. Selecting a tolerant longevity element may include selecting the second longevity element that is compatible with an ADME factor as the tolerant longevity element. In an embodiment, the computing device may select a tolerant longevity element by identifying a second longevity element compatible with the ADME factor. Computing device may select the second longevity element as a tolerant longevity element.

Alternatively or additionally, and still referring to FIG. 8, the computing device may display the second longevity element to the user. A user may include any human being. A user may be a family member or an informed advisor of a user. The second longevity element may be displayed as a digital communication which may include but not limited to an email message, a text message, or the like. The second longevity element may be displayed as a Uniform Resource Locator ("URL") address, a hyperlink, or the like. In a non-limiting examples, as diabetic user who is also asthmatic may need to take prednisone to control the asthma. A tolerant longevity element 180 such as Prednisone may cause computing device 104 to identify a second longevity element 132 such as Albuterol based on the ADME factor for Prednisone. Albuterol may be displayed in the user's mobile device.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
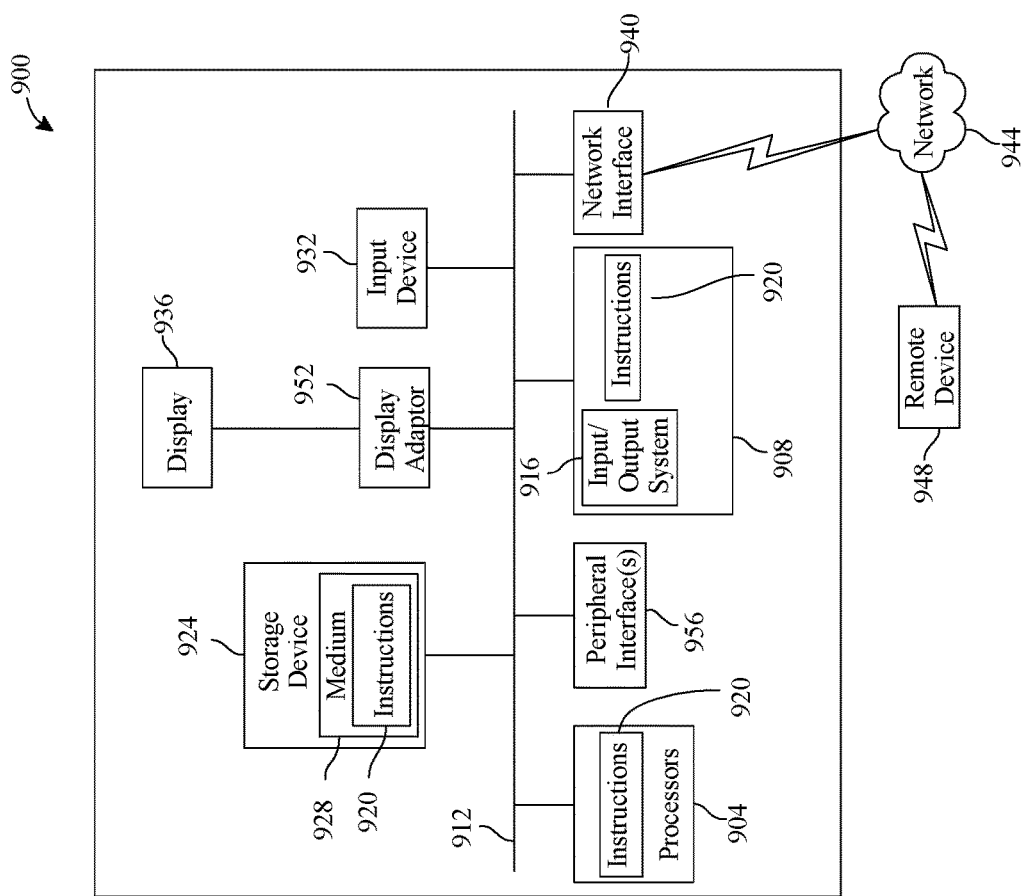
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Memory 908 may include various components (e.g., machine-readable media) including, but not limited to, a random access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 836 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for optimizing supplement decisions, the system comprising a computing device, the computing device further configured to:
receive a longevity inquiry from a remote device;
retrieve a first biological extraction from a user database, wherein the first biological extraction comprises a gut-wall body measurement related to a stool test result measuring a presence of a disease state;
identify a first longevity element associated with a user as a function of the longevity inquiry and the first biological extraction;
correlate a genetic marker from the first biological extraction with an ADME (Absorption, Distribution, Metabolism, and Excretion) model using a genetic classifier, wherein the genetic classifier is trained using training data, wherein the training data is updated based on at least a previously selected ADME model, such that the genetic classifier is customized to the user, wherein the genetic marker comprises a molecular marker configured to detect a variation of a nucleotide change, and wherein the nucleotide change comprises deletion, duplication, inversion, or insertion;
select the ADME model as a function of the first biological extraction and the genetic marker;
generate a machine-learning algorithm utilizing the selected ADME model that inputs the longevity element associated with the user as an input and outputs an ADME factor, wherein the ADME factor includes an absorption rate of the longevity element and the ADME factor is utilized by the machine-learning algorithm to compare longevity elements and select the longevity element the user is most tolerant of;
identify a second longevity element compatible with the ADME factor as a function of the first longevity element; and
select the second longevity element as a tolerant longevity element.

2. The system of claim 1, wherein receiving the longevity inquiry from a remote device further comprises receiving at an image device located on the computing device a wireless transmission from the remote device containing a photograph of a longevity element.

3. The system of claim 1, wherein identifying the first longevity element associated with the user further comprises:
receiving dietary training data wherein dietary training data includes a plurality of biological extractions and a plurality of correlated longevity elements;
generating using a first machine learning algorithm a dietary model relating biological extractions to longevity elements;
receiving a second biological extraction; and
outputting the first longevity element using the first machine learning algorithm and the second biological extraction.

4. The system of claim 3, wherein the first machine learning algorithm further comprises a supervised machine-learning algorithm.

5. The system of claim 1, wherein selecting an ADME model further comprises:
identifying a genetic marker contained within a third biological extraction;
generating using genetic training data including a plurality of genetic markers and a plurality of correlated ADME models, and using a classification algorithm, a genetic classifier, wherein the genetic classifier inputs a genetic marker and outputs an ADME model; and
selecting an ADME model as a function of generating the genetic classifier.

6. The system of claim 1, wherein selecting the ADME model further comprises:
retrieving a fourth biological extraction from the user database wherein the fourth biological extraction further comprises a genetic marker containing an ADME marker; and
locating an ADME model containing the ADME marker.

7. The system of claim 1, wherein the computing device is further configured to identify the second longevity element compatible with the ADME factor as a function of the first longevity element by:
identifying a first active ingredient contained in the first tolerant longevity element; and
identifying a second longevity element containing a second active ingredient, wherein the first active ingredient relates to the second active ingredient.

8. The system of claim 7, wherein the computing device is further configured to eliminate the first longevity element.

9. The system of claim 1, wherein the computing device is further configured to select the second longevity element as a tolerant longevity element by:
identifying a second longevity element compatible with the ADME factor; and
selecting the second longevity element as a tolerant longevity element as a function of the identification.

10. The system of claim 1, wherein the computing device is further configured to display the second longevity element to the user.

11. A method of optimizing supplement decisions, the method comprising:
receiving by a computing device a longevity inquiry from a remote device;
retrieving by the computing device a first biological extraction from a user database, wherein the first biological extraction comprises a gut-wall body measurement related to a stool test result measuring a presence of a disease state;
identifying by the computing device a longevity element associated with a user as a function of the longevity inquiry and the first biological extraction;
correlating a genetic marker from the first biological extraction with an ADME (Absorption, Distribution, Metabolism, and Excretion) model using a genetic classifier, wherein the genetic classifier is trained using training data, wherein the training data is updated based on at least a previously selected ADME model, such that the genetic classifier is customized to the user, wherein the genetic marker comprises a molecular marker configured to detect a variation of a nucleotide change, and wherein the nucleotide change comprises deletion, duplication, inversion, or insertion;
selecting by the computing device the ADME model as a function of the first biological extraction and the genetic marker;
generating, by the computing device, a machine-learning algorithm utilizing the selected ADME model that inputs the longevity element associated with the user as an input and outputs an ADME factor, wherein the ADME factor includes an absorption rate of the longevity element and the ADME factor is utilized by the machine-learning algorithm to compare longevity elements and select the longevity element the user is most tolerant of;

identifying a second longevity element compatible with the ADME factor; and selecting the second longevity element as a tolerant longevity element.

12. The method of claim 11, wherein receiving the longevity inquiry from a remote device further comprises receiving at an image device located on the computing device a wireless transmission from the remote device containing a photograph of a longevity element.

13. The method of claim 11, wherein identifying the first longevity element associated with the user further comprises:

receiving dietary training data wherein dietary training data includes a plurality of biological extractions and a plurality of correlated longevity elements;

generating using a first machine learning algorithm a dietary model correlating biological extractions with longevity elements;

receiving a second biological extraction; and outputting the first longevity element using the first machine learning algorithm.

14. The method of claim 13, wherein the first machine learning algorithm further comprises a supervised machine-learning algorithm.

15. The method of claim 11, wherein selecting the ADME model further comprises:

identifying a genetic marker contained within a third biological extraction;

generating using genetic training data including a plurality of genetic markers and a plurality of correlated ADME models, and using a classification algorithm, a genetic classifier, wherein the genetic classifier inputs a genetic marker and outputs an ADME model; and selecting an ADME model as a function of generating the genetic classifier.

16. The method of claim 11, wherein selecting the ADME model further comprises:

retrieving a fourth biological extraction from the user database wherein the biological extraction further comprises a genetic marker containing an ADME marker; and locating an ADME model containing the ADME marker.

17. The method of claim 11, wherein identifying a second longevity element compatible with the ADME factor as a function of the first longevity element further comprises:

identifying a first active ingredient contained in the first tolerant longevity element; and identifying a second longevity element containing a second active ingredient, wherein the first active ingredient relates to the second active ingredient.

18. The method of claim 17, wherein the method further comprises eliminating the first longevity element.

19. The method of claim 11, further comprising selecting a tolerant longevity element by:

identifying a second longevity element compatible with the ADME factor; and selecting the second longevity element as a tolerant longevity element.

20. The method of claim 19, further comprising displaying the second longevity element to the user.

* * * * *